United States Patent [19]

Nevell

[11] Patent Number: 4,822,277

[45] Date of Patent: Apr. 18, 1989

[54] ORTHODONTIC TRIVIDER

[76] Inventor: Vincent J. Nevell, 164 Edinburgh Street, Coffs Harbour Jetty, N.S.W., Australia

[21] Appl. No.: 132,966

[22] Filed: Dec. 15, 1987

[30] Foreign Application Priority Data

Dec. 22, 1986 [AU] Australia .............................. PH9618
May 11, 1987 [AU] Australia .............................. PI1844
Sep. 18, 1987 [AU] Australia .............................. PI4436

[51] Int. Cl.⁴ .............................................. A61C 7/00
[52] U.S. Cl. ...................................................... 433/3
[58] Field of Search ................................ 433/6, 3, 159

[56] References Cited

U.S. PATENT DOCUMENTS 3,686,762 8/1972 Sutter ...................................... 433/3
4,035,919 7/1977 Cusato ................................... 433/3
4,725,228 2/1988 Andrews .............................. 433/72

Primary Examiner—Robert Peshock
Attorney, Agent, or Firm—Gausewitz, Carr & Rothenberg

[57] ABSTRACT

An orthodontic apparatus is disclosed comprising a divider like device with three arms. The outer arms operate in normal fashion while the central arm is coupled to the adjusting wheel so that its relative position with respect to the outer arm is constant. The central arm has a bracket retaining reverse tweezer arrangement for holding and positioning orthodontic brackets on teeth. In use the outer arms are located on either side of the tooth and the central arm locates the bracket in the correct position for fixing to the tooth.

11 Claims, 2 Drawing Sheets

U.S. Patent   Apr. 18, 1989   Sheet 1 of 2   4,822,277

ORTHODONTIC TRIVIDER

The present invention relates to the application of orthodontic bands and brackets to teeth and more particularly to apparatus for use in the application of such bands and brackets.

Orthodontic brackets for teeth may be bonded directly to the tooth or applied using a band to which the bracket is welded and which band is cemented to the tooth.

In the former case the apparatus actually applies the bracket in the correct position and steadies it while the adhesive sets.

In the latter the apparatus acts as a guide to the correct placement of the band so the bracket is in correct alignment and position.

In using these banding techniques a bracket usually square or rectangular in shape is attached to individual teeth. Each bracket normally has a vertical channel and a horizontal channel for engagement with an arch wire. The brackets vary in size according to the tooth to which they are to be attached.

It is desirable when attaching the brackets that the vertical channel be aligned with the clinical long axis of the crown of the tooth. The horizontal channel has its angle relative to the vertical channel predetermined and is set in place with the alignment of the vertical channel.

The present invention seeks to provide apparatus which will assist the orthodontist in accurate placement of the above described brackets in relation to a tooth.

According to the invention there is provided orthodontic apparatus comprising:

a pair of arms co-extending from a hinge at one end thereof, a screw member spaced from said hinge and threadingly connecting said arms, a manually rotatable wheel fixed to the mid-position of said screw member for rotation thereof.

said screw member having oppositely-handed threads on each side of said wheel such that rotation thereof causes said arms to move inward or outward with respect to each other, a further arm, attached to said hinge and extending between said pair of arms, coupled to said wheel so as to maintain a fixed position relative to the positions of each of said pair of arms.

For preference, said further arm is arranged to maintain a position mid-way between each of said pair of arms and is provided with bracket retaining means at its end remote from said hinge. Preferably, spring means are provided to bias said pair of arms towards a separated position.

A preferred embodiment of the invention will now be described, by way of example only, with reference to the accompanying drawings in which.

Figure 1:
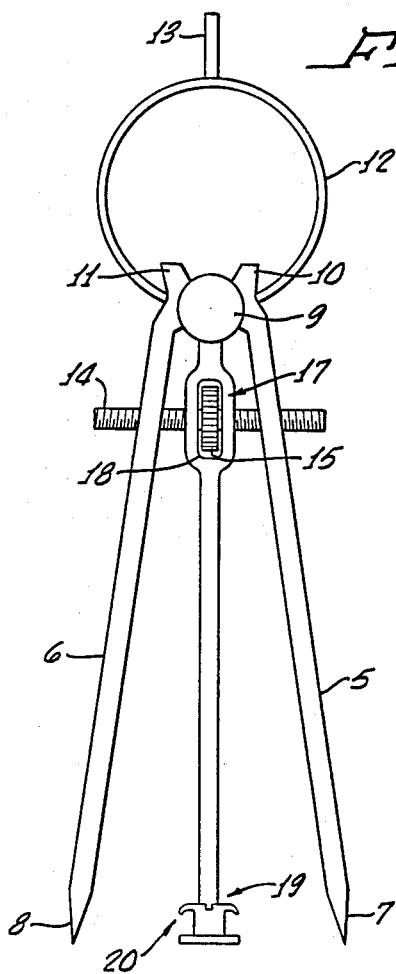
FIG. 1 shows a elevation of the orthodontic apparatus according to the invention.
Figure 2:
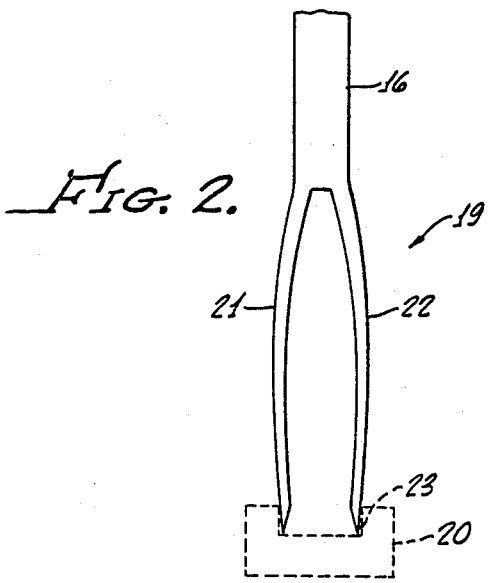
FIG. 2 shows an enlarged side elevation view of the bracket retaining means of FIG. 1.

Referring to FIGS. 1 and 2 of the drawings, the orthodontic apparatus consists of a pair of arms 5 and 6 having pointed ends 7 and 8. One end 8, is preferably flattened to allow it to lie against the biting edge of a tooth. The ends of the arms remote from said points are hinged by bracket 9 and have extensions 10 and 11 adapted to engage a bow spring 12 which biases said arms to a separated position by applying inward pressure to said extensions. A handle 13 is attached to the centre of the bow spring 12 to enable the apparatus to be held.

A screw member 14 threadingly engages each arm 5 and 6 and is rotated by a knurled wheel 15 attached at the centre thereof. The screw member has threads of opposite-hand on each side of said wheel 15 so that rotation of said wheel and screw member causes said arms to move inwardly or outwardly with respect to each other dependent on the direction of rotation of said wheel 15.

A central arm 16 is positioned intermediate said pair of arms 5 and 6 and attached at one end to said bracket 9. Arm 16 has two slots 17 and 18 provided therein corresponding to the position of said wheel 15. Slot 17 allows said screw member to pass through the central arm and the other slot 18 to closely accommodate said wheel.

The central arm 16 is provided with a bracket retaining means 19, shown in detail in FIG. 2, positioned at the end of the arm remote from bracket 9 and aligned substantially with the pointed ends of arms 5 and 6. An orthodontic bracket 20 is shown held by the retaining means 19.

The retaining means 19 comprises a reverse tweezer arrangement wherein the arm 16 is divided into two further arms 21 and 22 formed of a resilient material so that they are normally biased to be separated from one another. When closed they fit into a slot or cavity 23 provided in the orthodontic bracket 20 and spring outwardly to hold the bracket in position.

Figure 3:
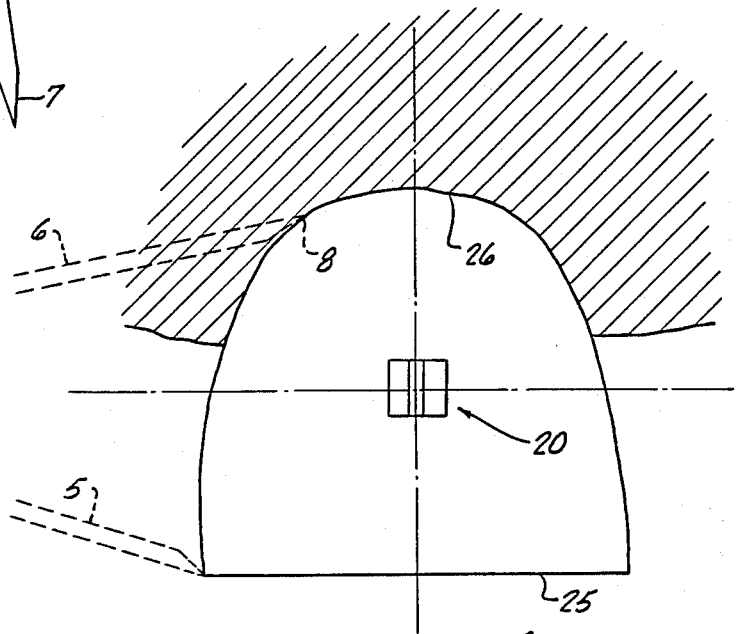
FIG. 3 shows a elevation of a typical tooth with an orthodontic bracket in position.

Referring to FIG. 3 a front elevation of a tooth is shown with a bracket 20 in position. The arms 5 and 6 of the apparatus according to the invention are adjusted such that one arm is positioned on the biting edge 25 of the tooth and the other on the gingival margin (gum) 26, the central arm 16 then positions the bracket 20 accurately on the clinical long axis of the tooth crown.

Figure 4:
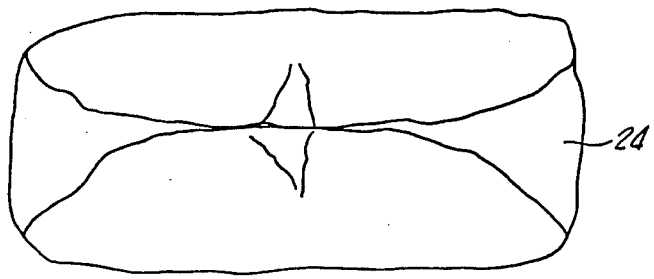
FIG. 4 shows a plan view of the biting surface of a posterior tooth.

The apparatus may also be used to relate the horizontal channel of the bracket 20 to the marginal ridge of the tooth 24. FIG. 4 shows a plan view of the biting surface of a posterior tooth. In this case, the arms 5 and 6 may be cranked to enable access to the tooth.

Figure 5A:
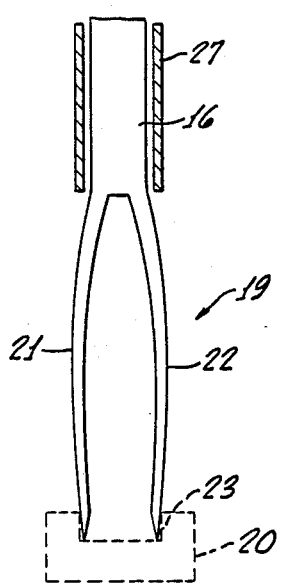
FIGS. 5A and 5B show an enlarged side elevation view of an alternative embodiment of the bracket retaining means of FIG. 2.
Figure 5B:
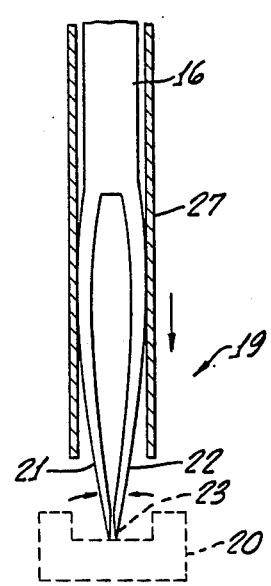

Referring to FIGS. 5A and 5B, an alternative embodiment of the bracket retaining means is shown. The tweezer arrangement shown in FIG. 2 is provided with a spring-loaded tubular sleeve 27 which slides two and fro along leg 16. In its retracted position (see FIG. 5A) the sleeve allows the tweezer arm 21 and 22 to spring apart and hold the bracket 20 in position. When the sleeve is slid downwardly over the tweezer arms (see FIG. 5B) it forces the arms inwardly compressing the tweezer and releasing the bracket.

Figure 6:
FIG. 6 shows a side elevation view of a tweezer arm of FIGS. 5A and 5B.

FIG. 6 shows the tweezer arms 21 and 22 with a notch 28 provided in their tips. This notch enables the tweezer to sit over a full banding set-up with the arch wire in place to enable checking of existing brackets and re-bonding of loosened brackets.

Figure 7:
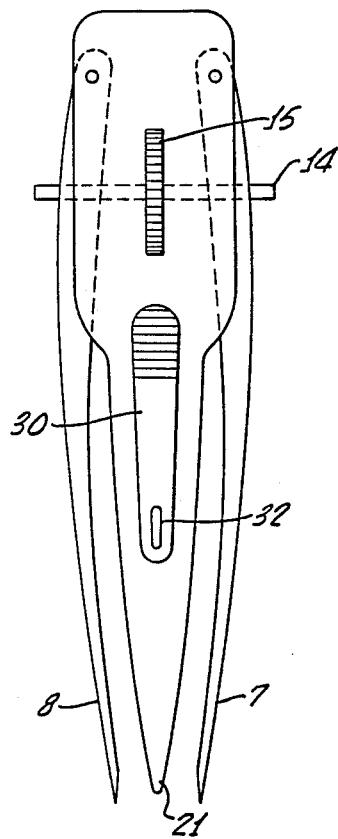
FIG. 7 shows a plan view of a further embodiment of the trivider according to the invention.
Figure 8:
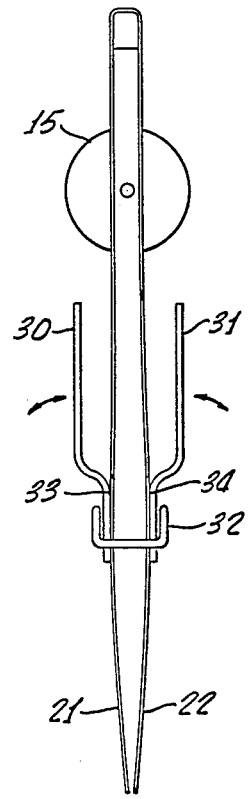
FIG. 8 shows a side elevation view of the trivider of FIG. 7.

Referring to FIGS. 7 and 8 a further arrangement for operating the tweezer arms 21 and 22 is shown. A further pair of lever arms 30 and 31 are attached to the outer sides of tweezer arms 21 and 22 respectively by a yoke 32 which extends through and between said tweezer arms. The yoke 32 fixedly clamps the lever arms to the tweezer arms. The lever arms 30 and 31 are bowed outwardly at pressure points 33 and 34 respectively.

In operation, the lever arms 30 and 31 are pressed inwardly towards each other applying a force at points 33 and 34 to the tweezer arms causing them to move together. The lever arms are biased outwardly by the resilience of the tweezer arms. The lever arms provide an additional mechanical advantage and thus enable the bias force of the tweezer arms to be greater without reducing ease of operation. The increased bias force provides a more positive engagement of the tweezer arms with the bracket 20.

It will be apparent to those persons skilled in the art that the invention is not limited to the specific embodiments described and further embodiments are possible without departing from the spirit or scope of the invention described.

I claim:

1. Orthodontic apparatus comprising:
   a pair of arms co-extending from a hinge at one end thereof,
   a screw member spaced from said hinge and threadingly connecting said arms,
   a manually rotatable wheel fixed to the mid-portion of said screw member for rotation thereof,
   said screw member having oppositely-handed threads on each side of said wheel such that rotation thereof causes said arms to move inward or outward with respect to each other,
   a further arm, attached to said hinge and extending between said pair of arms, coupled to said wheel so as to maintain a fixed position relative to the positions of each of said pair of arms,
   said further arm being provided with bracket retaining means at its end remote from said hinge.

2. Orthodontic apparatus comprising:
   a pair of arms co-extending from a hinge at one end thereof,
   spring means connecting said pair of arms to bias them towards a separated position,
   a screw member spaced from said hinge and threadingly connecting said arms,
   a manually rotatable wheel fixed to the mid-portion of said screw member for rotation thereof,
   said screw member having oppositely-handed threads on each side of said wheel such that rotation thereof causes said arms to move inward or outward with respect to each other,
   a further arm, attached to said hinge and extending between said pair of arms, coupled to said wheel so as to maintain a fixed position relative to the positions of each of said pair of arms, said further arm being provided with bracket retaining means at the end remote from said hinge.

3. Orthodontic apparatus according to claim 1 wherein said bracket retaining means comprises tweezer means consisting of a pair resilient arm portions connected at one end thereof and normally biassed to a separated position and adapted to fit within a slot in an orthodontic bracket and spring outwardly to engage and retain said bracket.

4. Orthodontic apparatus according to claim 3 wherein said tweezer means further includes a tubular sleeve sized to slidably engage said resilient arm portions and move them towards each other, said sleeve being slidable to and fro along said further arm.

5. Orthodontic apparatus according to claim 3 wherein the tips of said resilient arm portions are each provided with a transverse notch.

6. Orthodontic apparatus according to claim 3 wherein said tweezer means further includes a yoke extending between said resilient arm portions, and a pair of lever arms fulcrumed respectively to each said arm portion by said yoke, said lever arms being bowed outwardly from said resilient arm portions to provide an engagement section which presses inwardly upon said arms portions as said lever arms are brought towards one another.

7. Orthodontic apparatus comprising:
   a pair of arms co-extending from a hinge at one end thereof,
   a screw member spaced from said hinge and threadingly connecting said arms,
   a manually rotatable wheel fixed to the mid-portion of said screw member for rotation thereof,
   said screw member having oppositely-handed threads on each side of said wheel such that rotation thereof causes said arms to move inward or outward with respect to each other,
   a further arm, attached to said hinge and extending between said pair of arms, coupled to said wheel so as to maintain a fixed position relative to the positions of each of said pair of arms,
      said further arm being coupled to said wheel at a point such that said fixed position is mid-way between each of said pair of arms,
      said further arm being provided with bracket retaining means at its end remote from said hinge.

8. Orthodontic apparatus according to claim 7 wherein said bracket retaining means comprises tweezer means consisting of a pair resilient arm portions connected at one end thereof and normally biassed to a separated position and adapted to fit within a slot in an orthodontic bracket and spring outwardly to engage and retain said bracket.

9. Orthodontic apparatus according to claim 8 wherein said tweezer means further includes a tubular sleeve sized to slidably engage said resilient arm portions and move them towards each other, said sleeve being slidable to and fro along said further arm.

10. Orthodontic apparatus according to claim 8 wherein the tips of said resilient arm portions are each provided with a transverse notch.

11. Orthodontic apparatus according to claim 3 wherein said tweezer means further includes a yoke extending between said resilient arm portions, and a pair of lever arms fulcrumed respectively to each said arm portion by said yoke, said lever arms being bowed outwardly from said resilient arm portions to provide an engagement section which presses inwardly upon said arms portions as said lever arms are brought towards one another.

* * * * *